United States Patent [19]

Vagt et al.

[11] Patent Number: 4,950,429

[45] Date of Patent: Aug. 21, 1990

[54] PREPARATION OF 6-AMINOCAPROIC ACID

[75] Inventors: Uwe Vagt, Speyer; Rolf Fischer, Heidelberg; Franz Merger, Frankenthal; Hans-Martin Hutmacher, Ludwigshafen, all of Fed. Rep. of Germany

[73] Assignee: BASF Aktiengesellschaft, Ludwigshafen, Fed. Rep. of Germany

[21] Appl. No.: 327,432

[22] Filed: Mar. 23, 1989

Related U.S. Application Data

[63] Continuation of Ser. No. 7,472, Jan. 28, 1987, abandoned.

[30] Foreign Application Priority Data

Jan. 28, 1987 [DE] Fed. Rep. of Germany ....... 3602374

[51] Int. Cl.$^5$ .................. C07C 227/00; C07C 227/04
[52] U.S. Cl. .................... 260/404; 546/243; 562/553; 562/577; 560/175
[58] Field of Search ................ 562/577, 553; 260/404; 546/243

[56] References Cited

U.S. PATENT DOCUMENTS

| | | | |
|---|---|---|---|
| 2,129,317 | 9/1938 | Elger | 562/577 |
| 2,496,326 | 2/1950 | Albertson et al. | 546/243 |
| 2,505,459 | 4/1950 | Bruson et al. | 546/243 |
| 2,610,212 | 9/1952 | Floyd | 562/553 |
| 2,777,873 | 1/1957 | Hasek | 260/482 |
| 2,839,547 | 6/1958 | Berther | 562/553 X |
| 4,360,692 | 11/1982 | Kummer et al. | 560/175 |

FOREIGN PATENT DOCUMENTS

| | | | |
|---|---|---|---|
| 0031100 | 7/1981 | European Pat. Off. | 560/175 |
| 0091091 | 10/1983 | European Pat. Off. | 560/175 |
| 952442 | 3/1956 | Fed. Rep. of Germany | 562/533 |
| 61-27940 | 2/1986 | Japan | 562/577 |
| 1202875 | 8/1970 | United Kingdom | 562/553 |
| 2046253 | 11/1980 | United Kingdom | 562/533 |

OTHER PUBLICATIONS

Buehler, "Survey of Organic Syntheses", pp. 424 to 427 (1970).
Houben-Weyl, "Methoden Der Organischen Chemie", vol. XI/1, pp. 606 to 609 (1957).
Itin et al., Chemical Abstracts, vol. 52, 2056-2057 (1958).
Rabjohn, "Organic Syntheses", Collective vol. 4, pp. 39 to 42 (1963).
Shpital'nyi et al., Chemical Abstracts, vol. 53, 16005f (1959).
Theilheimer, "Synthetic Methods Der Organischen Chemie", vol. 4, p. 56, #159 (1950).
Vinnik et al., Chemical Abstracts; vol. 60, 387b,c (1964).
Wagmer et al., "Synthetic Organic Chemistry", pp. 662 to 663 (1953).
Wichterle, Chemical Abstracts, vol. 50, 10127b (1956).
Journal of the American Chemical Society, vol. 64, pp. 1416-1421, (1942) (Oxidative Cleavage of Cyclicα-Keto Alcohols by Means of Lead Tetraacetate), Baer.

*Primary Examiner*—Floyd D. Higel
*Attorney, Agent, or Firm*—Keil & Weinkauf

[57] ABSTRACT

6-Aminocaproic acid is prepared by
  (a) reacting a 5-formylvaleric acid ester with water in the presence of an acid agent at 30°-200° C. and
  (b) reacting the 5-formylvaleric acid thus obtained with excess ammonia and hydrogen in the presence of a hydrogenation catalyst and of a solvent which is inert under the reaction conditions at 50°-150° C. under superatmospheric pressure.

8 Claims, No Drawings

PREPARATION OF 6-AMINOCAPROIC ACID

This application is a continuation of application Ser. No. 007,472 filed on Jan. 28, 1987 now abandoned.

The present invention relates to a process for preparing 6-aminocaproic acid from 5-formylvaleric acid esters.

In a process described in J. Amer. Chem. Soc. 64 (1942), 1416 et seq., 5-formylvaleric acid is obtained by reacting 2-hydroxycyclohexanone with lead tetraacetate in glacial acetic acid. This process has the disadvantage that it requires expensive starting materials and only gives inadequate yields. An additional disadvantage is the inevitable production of lead compounds which must be disposed of. In another process, described in Chem. Ber. 72 (1939), 1194, 5-formylvaleric acid is obtained by reacting cyclohexanone with alkaline hydrogen peroxide. However, the selectivities achieved are low and the reaction times required are long. In a further process, described in European Patent Application 91,091, 5-formylvaleric acid is prepared by oxidizing cyclohexanone with molecular oxygen in the presence of homogeneous catalysts such as iron(III) chloride and thiourea. In this process, however, adequate selectivities are achieved only in the case of conversions of less than 50%. In addition, the homogeneously dissolved catalysts must be separated from the reaction mixture, which is expensive.

Japanese Patent Publication 21,138/66 discloses a process wherein δ-formylvaleric acid, ammonia and water as diluent are reacted at above 100° C. in the presence of hydrogen and hydrogenation catalysts. However, here the product is caprolactam.

It is an object of the present invention to provide a process for converting a 5-formylvaleric acid ester into 6-aminocaproic acid in a high yield and a short reaction time with little byproduct using an easily removed catalyst.

We have found that this object is achieved in a process for preparing 6-aminocaproic acid, which comprises (a) reacting a 5-formylvaleric acid ester with water in the presence of an acid agent at 30–200° C. and (b) reacting the 5-formylvaleric acid thus obtained with excess ammonia and hydrogen in the presence of a hydrogenation catalyst and of a solvent which is inert under the reaction conditions at 50–150° C. under superatmospheric pressure.

The novel process has the advantage that it is possible to prepare 6-aminocaproic acid from a 5-formylvaleric acid ester in a high yield in a simple manner. In addition, the novel process has the advantage that it takes a short time and produces few byproducts. The novel process has the further advantage that easily removed catalysts are used. The novel process is remarkable insofar as it was to be expected that in an acid medium 5-formylvaleric acid would undergo intermolecular or intramolecular aldol condensations (formation of five-membered rings). For instance, it is known from Houben-Weyl, Methoden der org. Chemie, Volume VII/1, page 87, that at adipaldehyde undergoes an intramolecular aldol condensation in an acid medium.

Preferred 5-formylvaleric acid esters for use in stage a are derived from alkanols of 1 to 12 carbon atoms, cycloalkanols of 5 to 7 carbon atoms, aralkanols of 7 or 8 carbon atoms or phenols of 6 to 8 carbon atoms. Particularly preferred starting materials are $C_1$–$C_4$-alkyl 5-valerates. Suitable starting materials are for example methyl 5-formylvalerate, ethyl 5-formylvalerate, n-propyl 5-formylvalerate, i-propyl 5-formylvalerate, n-butyl 5-formylvalerate, 2-ethylhexyl 5-formylvalerate, cyclohexyl 5-formylvalerate or phenyl 5-formylvalerate. Methyl 5-formylvalerate is of particular industrial importance. 5-Formylvaleric acid esters are readily accessible according to the process described in European Patent Application 31,000 by hydroformylation of 4-pentenoic acid esters.

In general, for every mole of 5-formylvaleric acid ester from 1 to 200 moles, in particular from 50 to 150 moles, of water a e employed. It is also possible to employ solvents which are inert under reaction conditions. Suitable solvents are, for example, hydrocarbons such as cyclohexane or toluene, halohydrocarbons such as dichloromethane or tetrachloromethane, ethers such as dioxane or diglyme. If solvents are used, the 5-formylvaleric acid esters are used in the form of a 1–90% strength by weight solution, in particular a 5–20% strength by weight solution.

The reaction s carried out at 30–200° C., advantageously at 50–120° C. In general the reaction is carried out under atmospheric pressure. However, it is also possible to employ slightly subatmospheric or superatmospheric pressure, for example up to 20 bar.

The reaction s carried out in the presence of acid agents. Suitable acid agents are, for example, sulfonic acids, Lewis acids, nonoxidizing mineral acids, lower fatty acids or strongly acid cation exchangers. Suitable acid agents are, for example, nonoxidizing mineral acids, such as sulfuric acid, hydrochloric acid, hydrobromic acid, sulionic acids, such as p-toluenesulfonic acid, Lewis acids such as boron trifluoride or zinc chloride, and also lower aliphatic carboxylic acids, such as formic acid, acetic acid or propionic acid, as well as strongly acid cation exchangers. These strongly acid cation exchangers are for example based on crosslinked polystyrene having sulfo groups or phenolic resins having sulfo groups or are acid zeolites.

Advantageously sulfonic acids, Lewis acids or nonoxidizing mineral acids are used in catalytic amounts, for example from 0.002 to 0.25 mole per mole of 5-formylvaleric acid ester. Aliphatic carboxylic acids are generally used in amounts of from 0.1 to 1 mole per mole of 5-formylvaleric acid ester.

Particular preference is given to using strongly acid cation exchangers.

The process can be carried out batchwise or, advantageously, continuously, for example in a stirred kettle cascade. In such a continuous process, it is expedient to separate the alcohol which is produced in the course of the hydrolysis continuously from the reaction mixture by distillation. In the event of using a strongly acid cation exchanger it is advantageous to carry out the reaction in such a wa) that the strongly acid cation exchanger is arranged in the form of a fixed bed, for example in a tubular reactor, and the reaction mixture is trickled over. In a particularly advantageous embodiment, the reaction mixture is initially trickled through a first reaction zone over a fixed bed of strongly acid cation exchanger and is then circulated in a second reaction zone over a fixed bed of strongly acid cation exchanger, the reaction mixture being removed at the rate at which it is fed in to the first zone. Advantageously, unconverted 5-formylvaleric acid ester is extracted with, for example, a hydrocarbon such as cyclohexane from the reaction mixture thus obtained and is expediently reused.

In another advantageous embodiment, the 5-formylvaleric acid ester and water are passed in excess through a column coated with strongly acid cation exchanger, alcohols are distilled off at the top end, and an aqueous solution of 5-formylvaleric acid is removed at the bottom end.

From the aqueous solution thus obtained it is possible to obtain 5-formylvaleric acid in pure form by distillation. Advantageously, the aqueous solution of 5-formylvaleric acid, which for example has a content of from 3 to 15% by weight, is used directly for preparing 6-aminocaproic acid.

In a second stage (stage b), the 5-formylvaleric acid thus obtained is then reacted with excess ammonia and hydrogen in the presence of a hydrogenation catalyst and of a solvent at 50–150° C. under superatmospheric pressure.

The 5-formylvaleric acid is generally used in the form of a 1–50% strength by weight, preferably 2–35% strength by weight, in particular 5–25% strength by weight, solution. The solution predominantly contains monomer and a little low molecular weight oligomeric 5-formylvaleric acid. Suitable solvents are, for example, water, monohydric or polyhydric alcohols of 1 to 5 carbon atoms, ethers, such as dioxane, tetrahydrofuran or diglyme, or mixtures thereof.

Preferably the solvent used is water. It has proved suitable in particular to use the aqueous solution of 5-formylvaleric ac d in the form in which it is obtained in stage a.

In general, for every mole of 5-formylvaleric acid, from 2 to 50 moles, in particular from 4 to 30 moles, of ammonia are used.

The reaction s carried out at 50–150° C., advantageously 70–130° C. In general a pressure of from 10 to 400 bar, advantageously from 20 to 300 bar, in particular from 50 to 250bar, is employed. Hydrogen is in general used in an amount of from 1 to 10 moles per mole of 5-formylvaleric ac d. Preferably the hydrogen is used in excess, for example 2–5 moles per mole of 5-formylvaleric acid.

Suitable hydrogenation catalysts are metals of group VIII of the Periodic Table, such as nickel catalysts, cobalt catalysts or noble metal catalysts, such as ruthenium, platinum or palladium. The catalysts may contain activating additives such as zirconium, manganese, copper or chromium. The catalysts can be used in the form of solid catalysts or deposited on carriers such as alumina, silica gel or active carbon. Skeleton catalysts are also suitable.

Suitable catalysts contain, for example, from 80 to 100% by weight of cobalt and/or nickel, based on the metal content of the catalyst. In addition to cobalt and/or nickel, the catalysts can also contain metals such as copper or chromium, for example up to 20% by weight on the metal content. The catalysts can be supported by carriers, for example silicates, aluminum phosphate, boron phosphate, alumina or active carbon. The metal content of the supported catalysts is expediently from 5 to 80% by weight, based on the total catalyst weight.

Other suitable catalysts are those which are obtained by calcining compounds of the formula I [(Mg$_a$Ni(II)$_b$Co(II)$_c$)Al$_2$CO$_3$(OH)$_{16}$×4H$_2$O, where a is a whole or decimal number from 0 to 4 and b and c are each a whole or decimal number from 0 to 6, with the proviso that 2×(a+b+c)=12, at 200–600° C. and subsequently reducing with hydrogen at elevated temperatures. Preferred starting materials are the following compounds of the formula I:

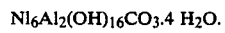

$Ni_6Al_2(OH)_{16}CO_3.4 H_2O.$

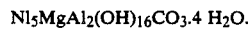

$Ni_5MgAl_2(OH)_{16}CO_3.4 H_2O.$

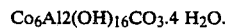

$Co_6Al_2(OH)_{16}CO_3.4 H_2O.$

$Co_5MgAl_2(OH)_{16}CO_3.4.H_2O.$

The compounds of the formula I are obtained for example as follows: nickel, aluminum, cobalt and magnesium, in the form of their water-soluble salts such as chlorides, sulfates or preferably nitrates, are dissolved together in water in a mixing ratio which is as close as possible to the desired composition of the catalyst and stoichiometrically conforms to the formula I.

The metal salt solution should in total be about from 0.5 to 3 molar, preferably from 1.0 to 2 molar, in metal ions. The solution is heated to 50–100° C., preferably 80–100° C., and in the course of 0.5–10, preferably 1–3, minutes is combined with an equivalent amount or preferably a small excess of a hot 1–3, preferably 1.5–2.5 molar solution of an alkali metal bicarbonate at 50–100° C., preferably 80–100° C. Advantageously the alkali metal bicarbonate is used in an excess of up to 20% by weight, preferably 0.5–3% by weight, based on the theoretical amount of bicarbonate. After the metal salt solution has been added, ie. after the two solutions have been combined, the mixture is expediently stirred for 10–30, preferably 15–20, minutes, and the resulting precipitate is then filtered off, washed with water and dried at 50–200° C., preferably 100–160° C. The basic carbonates are obtained in almost quantitative yields. Suitable alkali metal bicarbonates are in particular sodium bicarbonate or potassium bicarbonate. However, it is also possible to use ammonium bicarbonate in the precipitation. Similarly, it is also possible to use mixtures of the bicarbonates mentioned. In addition t is possible to effect the precipitation of the metal ions with solutions of alkali metal carbonates in sodium carbonate and/or potassium carbonate if carbon dioxide is passed into the alkali metal carbonate solution during the precipitation, which in effect likewise amounts to a precipitation with bicarbonate.

Advantageously the calcination conditions are 250–400° C., for example for 5–40, in particular 15–30, hours. Before the catalyst is actually used, it is reduced with hydrogen, advantageously at 180–500° C., preferably 250–450° C., for example in the course of 5–100 hours, advantageously 10–25 hours.

The hydrogenation is advantageously carried out with a residence time of from 1 to 120 minutes, in particular from 10 to 60 minutes. Furthermore, a weight hourly space velocity of from 0.2 to 2 kg of 5-formylvaleric acid per liter of catalyst per hour has proved suitable.

The reaction can be carried out batchwise, for example in a pressure vessel, or continuously in a reaction zone using a fixed bed catalyst in an immersed or trickle bed procedure. It has proved particularly advantageous to avoid backmixing during the reaction.

From the reaction mixture obtained, 6-aminocaproic acid, which is obtained as an inner salt, is separated off in a conventional manner, for example by crystallization.

The 6-aminocaproic acid prepared by the process of the invention is suitable for preparing caprolactam or directly for preparing nylons.

The process according to the invention is illustrated by the following Examples.

EXAMPLE 1

36 g of methyl 5-formylvalerate, 90 g of water and 0.5 g of sulfuric acid were heated under reflux for 3.5 hours, the methanol formed being distilled off continuously. Fractional vacuum distillation gave 18.5 g of 5-formylvaleric acid (yield 57% of theory).

Boiling point 106–112° C./1 mbar; $^{13}$C-NMR spectrum in D-chloroform: chemical shifts (relative to tetramethylsilane as interral standard): 21, 24, 34 and 44 ppm (4 methylene groups), 178 ppm (formyl group) and 203 ppm (carboxyl group).

EXAMPLE 2

36 g of methyl 5-formylvalerate, 90 g of water and 1 g of p-toluenesclfonic acid were heated under reflux for 8 hours, the methanol formed being distilled off continuously. Fractional vacuum distillation gave 13.3 g of 5-formylvaleric acid (yield 41% of theory).

EXAMPLE 3

36 g of methyl 5-formylvalerate, 90 g of water and 2 g of cation exchanger made of crosslinked polystyrene having sulfo groups were heated under reflux for 8.5 hours, the methanol formed being distilled off continuously. Fractional vacuum distillation gave 24 g of 5-formylvaleric acid (yield 74% of theory).

EXAMPLE 4

Methyl 5-formylvalerate (5-FVAE; 5–10 ml/h) and water (50–100 ml/h) were continuously pumped through two heatable jacketed steel pipe reactors (internal temperature 60–100° C.) which were packed with a cation exchanger made of crosslinked polystyrene having sulfo groups (reactor I: 100 ml of ion exchanger, no circulation; reactor II: 50 ml of ion exchanger, 0–30 l/h circulation). The outputs were analyzed by gas chromatography and found to contain the following amounts of 5-formylvaleric acid (5-FVA) and 5-FVAE:

| No. | Temp. | Circulation RII [l/h] | 5-FVA [% by weight] | 5-FVAE [% by weight] | Yield [% of theory] | Selectivity [%] |
| --- | --- | --- | --- | --- | --- | --- |
| 41 | 60° C. | 15 | 10.39 | 1.89 | 78 | 89 |
| 42 | 80° C. | 15 | 6.36 | 0.59 | 78 | 84 |
| 43 | 100° C. | 15 | 4.00 | 0.38 | 53 | 56 |

A portion of the reaction output (reaction temperature 60° C.) was fractionated under reduced pressure to give 75% of theory of 5-FVA of boiling point 102–123° C./1 mbar.

The reaction outputs were extracted with cyclohexane. The aqueous phases were found to contain, after the extraction, the following amounts of 5-FVA and 5-FVAE (gas chromatography):

| No. | 5-FVA [% by weight] | 5-FVAE [% by weight] |
| --- | --- | --- |
| 41 | 10.28 | 0.21 |
| 42 | 6.23 | 0.16 |
| 43 | 3.97 | <0.01 |

EXAMPLE 5

(a) 5-Formylvaleric acid by hydrolysis of methyl 5-formylvalerate

Methyl 5-formylvalerate (5-FVAE; 5 ml/h) and water (50 ml/h) were continuously pumped through two heatable jacketed steel pipe reactors (internal temperature 60° C.) which were packed with a strongly acid ion exchanger (reactor I: no circulation; reactor II: 15 l/h circulation).

The output was found by gas chromatography to contain the following amounts of 5-formylvaleric acid (5-FVA) and 5-FVAE:

| 5-FVA [% by weight] | 5-FVAE [% by weight] | Yield [% of theory] | Selectivity [%] |
| --- | --- | --- | --- |
| 7.03 | 0.80 | 78 | 85 |

The reaction output was extracted with cyclohexane. The aqueous phase was found by gas chromatography to contain, after the extraction, the following amounts of 5-FVA and 5-FVAE:

| 5-FVA [% by weight] | 5-FVAE [% by weight] |
| --- | --- |
| 6.23 | 0.04 |

(b) 6-Aminocaproic acid by aminating hydrogenation of 5-formylvaleric acid 100 ml of 5-formylvaleric acid solution in water (6.23% by weight of 5-FVA; reaction output from a) after the extraction of unconverted ester with cyclohexane) were pumped at 110° C./150 bar hydrogen into a suspension of 10 g of Ru-Zr catalyst (0.5% by weight of Ru and 1% by weight of Zr on alumina) in 60 g of a 12.5% strength aqueous ammonia in a 300 ml stirred steel autoclave, and the mixture was subsequently stirred at 110° C. for 2 hours.

The aminocaproic acid in the reaction output was determined by quantitative HPLC and found to correspond o a yield of 77% of theory.

EXAMPLE 6

100 ml of a 14.8% strength by weight 5-formylvaleric acid solution in water were pumped at 70–130° C./ 150 bar hydrogen into a suspension of the catalyst in an aqueous ammoniacal solution in a 300 ml stirred steel autoclave, and the mixture was subsequently stirred for 2 hours at said temperature.

The aminocaproic acid in the reaction output was determined by quantitative HPLC.

| No. | Temp. [°C.] | Catalyst | Yield of 6-ACA [% of theory] |
| --- | --- | --- | --- |
| 6.1 | 70 | 2 g RANEY nickel | 57 |
| 6.2 | 110 | 2 g RANEY cobalt | 57 |
| 6.3 | 130 | 2 g RANEY nickel | 57 |

COMPARATIVE EXAMPLE 10 g of trimeric 5-formylvaleric acid, 60 g of 12.5% strength aqueous ammonia and 2 g of RANEY nickel were stirred at 110° C./150 bar hydrogen in a 300 ml stirred steel autoclavs for 5 hours.

The reaction output was found by quantitative HPLC to contain 31% of theory of 6-aminocaproic acid.

We claim:
1. A process for preparing 6-aminocaproic acid by
(a) reacting a 5-formylvaleric acid ester with water in the presence of strongly acid cation exchangers at 50 to 120° C., while continuously separating the alcohol produced int the course of the hydrolysis from the reaction mixture by distillation and
(b) reacting the resulting 5-formylvaleric acid, in the form of an aqueous solution obtained from step (a), with excess ammonia and hydrogen in the presence of a hydrogenation catalyst at 70 to 130° C. under super-atmospheric pressure.

2. The process of claim 1, wherein 50–150 moles of water are used per mole of 5-formylvaleric acid ester.

3. The process of claim 1, wherein 5-formylvaleric acid ester is passed with water through two reaction zones connected in series which are packed with strongly acid cation exchangers, in the second reaction zone the reaction mixture being circulated and the aqueous solution removed being extracted with a hydrocarbon.

4. The process of claim 1, wherein from 4 to 30 moles of ammonia are used per mole of 5-formylvaleric acid.

5. The process of claim 1, wherein the reaction in step (b) is carried out at a pressure of from 50 to 250 bar.

6. The process of claim 1, wherein a ruthenium, platinum or palladium catalyst is used as the hydrogenation catalyst in step (b).

7. The process of claim 1, wherein a ruthenium-zirconium catalyst is used as the hydrogenation catalyst in step (b).

8. The process of claim 1, wherein a Raney nickel catalyst is used as the hydrogenation catalyst in step (b).

* * * * *